United States Patent [19]

Govindan et al.

[11] Patent Number: 5,426,190

[45] Date of Patent: Jun. 20, 1995

[54] PREPARATION OF N-(ORGANOCARBONYLOXY)-SUCCINIMIDE DERIVATIVES OF N-HYDROXYSUCCINIMIDE

[75] Inventors: Cheruthur Govindan, Murrysville; Suresh B. Damle, Pittsburgh, both of Pa.

[73] Assignee: PPG Industries, Inc., Pittsburgh, Pa.

[21] Appl. No.: 260,643

[22] Filed: Jun. 16, 1994

[51] Int. Cl.$^6$ .......................................... C07D 207/404
[52] U.S. Cl. ...................................... 548/542; 548/545
[58] Field of Search ............................... 548/542, 545

[56] References Cited

U.S. PATENT DOCUMENTS 2,816,111  12/1957  Wegler et al. .................... 260/293.4

FOREIGN PATENT DOCUMENTS

0451519A1  3/1991  European Pat. Off. .
4014272A1  5/1990  Germany .

OTHER PUBLICATIONS

G. W. Anderson et al, "The Use of Esters of N-Hydroxysuccinimide in Peptide Synthesis", J. Am. Chem. Soc., 86, pp. 1838–1842, (1963).
Kirk–Othmer Encyclopedia of Chemical Technology, 2nd ed. (1965), vol. 6, p. 506.
CRC Handbook of Chemistry and Physics, 65th ed. (1984), pp. C-669 thru C-704.
104654y, "Simple synthesis of N-hydroxysuccinimide", Chemical Abstracts, (1967), p. 977.

*Primary Examiner*—David B. Springer
*Attorney, Agent, or Firm*—George D. Morris

[57] ABSTRACT

Acylated derivatives of N-hydroxysuccinimide are produced from succinic anhydride, hydroxylamine, and acylating agent without purification of the intermediate N-hydroxysuccinimide.

16 Claims, No Drawings

PREPARATION OF N-(ORGANOCARBONYLOXY)-SUCCINIMIDE DERIVATIVES OF N-HYDROXYSUCCINIMIDE

The acylated derivatives of N-hydroxysuccinimide are useful reagents for the syntheses of many compounds. The carbonate esters are useful for providing carbamate (viz., urethane) groups to compounds. For example N-(benzyloxycarbonyloxy)succinimide [CAS 13139-17-8] ("BCS") and N-(9-fluorenylmethoxycarbonyloxy)succinimide [CAS 82911-69-1] ("FCS") are used as reagents for the introduction of the benzyloxycarbonyl and the 9-fluorenylmethoxycarbonyl protecting groups, respectively, in amino acids and antibiotics. Carboxylic acid esters of N-hydroxysuccinimide are useful activated esters for use in organic syntheses. For example, N-(butanoyloxy)succinimide [CAS 70741-39-8], N-(hexanoyloxy)succinimide [CAS 22102-92-7], N-(octanoyloxy)succinimide [CAS 14464-30-3], N-(decanoyloxy)succinimide [CAS 22102-66-5], N-(dodecanoyloxy)succinimide [CAS 14565-47-0], and N-(tetradecanoyloxy)succinimide [CAS 69888-86-4] are used to convert amine functionality to amide functionality in amino acids, peptides, and proteins.

These acylated derivatives are ordinarily prepared by reacting acylating agents with N-hydroxysuccinimide [CAS 6066-82-6] ("NHS"). Efficiency in the preparation of NHS is accordingly an important feature in an integrated process where NHS and an acylated derivative of NHS are sequentially produced.

One known method for the preparation of NHS is described in U.S. Pat. No. 2,816,111. According to that method, succinic anhydride [CAS 108-30-5] ("SA") is reacted with free hydroxylamine [CAS 7803-49-8] in methanol and then the resulting reaction mixture is heated under vacuum at 160° C. for 1½ hours. The product is extracted out with ethyl acetate and then purified by crystallization. Large quantities of solvents are needed for the extraction. The Field is about 53%. The method is undesirable because the yield is low, because handling large quantities of methanol presents safety and environmental problems, and because handling large quantities of extraction solvents also presents safety and environmental problems.

Anderson, Zimmerman, and Callahan, *Journal of the American Chemical Society*, 86, 1839-1842 (1964) describe the preparation of NHS by the fusion of hydroxylamine hydrochloride [CAS 5470-11-1] and succinic anhydride at 125° C. to 160° C. The product is then worked up with large quantities of solvents. Yield is about 44%. This method is undesirable because the yield is low, because fusion provides a yellow material, and because handling large quantities of extraction solvents presents safety and environmental problems.

A third method is described in *Chemical Abstracts*, 66, Abstract 104654v (1967). In this method succinic anhydride is reacted with hydroxylamine in a mixed solvent system consisting of water and dioxane. After reaction, the product is again heated at 160° C. and then extracted with large quantities of solvents, treated with carbon, and then crystallized. Yield is 75%. This method is undesirable because the yield is low, because the use of dioxane gives rise to health and safety problems, and because handling large quantities of extraction solvents presents safety and environmental problems. Moreover, the nature of the reaction in methods involving the preparation of NHS from succinic anhydride and hydroxyl amine in water is such that the conversion of some of the succinic anhydride to succinic acid is unavoidable. This succinic acid is present in the crude reaction product as an impurity. In most cases the succinic acid constitutes from 5 to 10 percent by weight of the NHS in the crude reaction product. In the subsequent purification procedures involving large quantities of organic solvents, a loss in yield of NHS based on succinic anhydride occurs. This loss in yield is usually in the range of from 15 to 20 percent, and hence is quite significant.

The reaction of commercially pure NHS, base, and acylating agent in a two-phase liquid system to produce N-(organocarbonyloxy)succinimide, is itself known. However, since these reactions use commercially pure NHS and since substantial amounts of NHS have been lost in producing the commercially pure NHS, the yield of N-(organocarbonyloxy)succinimide based on succinic anhydride, is low.

It has now been found that N-(organocarbonyloxy)succinimide can be produced from crude NHS. By proceeding in this manner, much of the NHS which would otherwise have been lost during purification of the NHS can be utilized in producing the ultimate N-(organocarbonyloxy)succinimide product.

Accordingly, the invention is a method for producing N-(organocarbonyloxy)succinimide comprising: (a) reacting succinic anhydride with hydroxylamine in water to form a reaction mixture; (b) heating the reaction mixture and removing water to produce solid comprising N-hydroxysuccinimide and a contaminating amount of succinic acid; (c) dissolving the solid in water to form an aqueous solution comprising dissolved N-hydroxysuccinimide and dissolved succinic acid; (d) combining substantially water-immiscible inert organic solvent and the aqueous solution to form a two-phase liquid system having an organic phase and an aqueous phase comprising the dissolved N-hydroxysuccinimide and the dissolved succinic acid; (e) adding base and at least one acylating agent represented by the formula

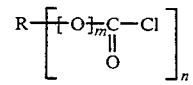

to the liquid system; and (f) reacting dissolved N-hydroxysuccinimide, the base, and the acylating agent in the liquid system to produce N-(organocarbonyloxy)succinimide represented by the formula

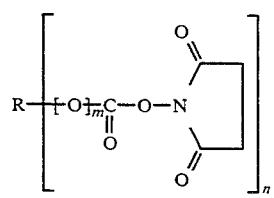

which accumulates in the organic phase; wherein R is an organo group, m is 0 or 1, and n is the valence of R.

R may be any of a wide variety of organo groups. It may be a hydrocarbon group or it may contain one or more other atoms in addition to carbon and hydrogen. The other atoms may be hetero atoms, substituents, and/or components of substituents. The valence of R is usually 1, 2, or 3, although it can be higher. Often the valence of R is 1 or 2. A valence of 1 is preferred. Examples of organo groups that may be employed include alkyl, cycloalkyl, aryl, aralkyl, alkoxy, aryloxy, aralkoxy, alkanediyl, alkylidene, cycloalkanediyl, cycloalkanediylbis(alkanediyl), arylene, arylenebis(alkanediyl), alkylidenebis(arylene), and alkanediylbis(arylene). Further examples include fused ring groups, spiro groups, and bridged ring groups.

In most instances the organo group contains from 1 to 18 carbon atoms. Often the organo group contains from 1 to 10 carbon atoms. In many instances the organo group contains from 1 to 8 carbon atoms. When the organo group is aliphatic, it usually contains from 1 to 18 carbon atoms; from 6 to 18 carbon atoms is preferred. When the organo group comprises one or more cycloaliphatic rings, it usually contains from 3 to 18 carbon atoms; from 6 to 10 carbon atoms is preferred. When the organo group comprises one or more aromatic rings, it usually contains from 6 to 18 carbon atoms; from 6 to 15 carbon atoms is preferred.

The reaction of step (a) is a liquid phase reaction.

The hydroxylamine which is reacted with succinic anhydride in step (a) may be introduced to the reaction mixture as free hydroxylamine or it may be produced in situ from hydroxylamine salt and base. Examples of suitable hydroxylamine salts that can be used include hydroxylamine sulfate, hydroxylamine hydrochloride, hydroxylamine hydrobromide, hydroxylamine nitrate, and hydroxylamine phosphate. A mixture of two or more hydroxylamine salts can be used. Examples of bases that can be used include alkali metal hydroxide, alkaline earth metal hydroxide, alkali metal carbonate, and alkali metal bicarbonate. A single base or a mixture of bases can be used as desired. The preferred bases are sodium hydroxide and potassium hydroxide.

Use of hydroxylamine salt and base to produce free hydroxylamine results in the production of by-product salt which accumulates in the reaction mixture and eventually appears as a contaminant in the solid produced in step (b). It has been found that the presence of such by-product salt is not detrimental to the practice of the present invention.

The molar ratio of hydroxylamine (whether introduced as free hydroxylamine or as hydroxylamine salt) to succinic anhydride introduced to the reaction mixture may be widely varied. Either reactant may be in excess or they may be introduced in a stoichiometric amount. Usually the molar ratio of hydroxylamine to succinic anhydride introduced to the reaction mixture is in the range of from 0.8:1 to 1.2:1. Often the molar ratio is in the range of from 0.9:1 to 1.1:1. From 0.95:1 to 1.05:1 is preferred.

The amount of water present is susceptible to very wide variation. In general, the amount of water present should be sufficient to permit a liquid phase reaction to proceed. The maximum amount of water is not limited by theory, but by practical considerations such as the size of equipment and the costs of handling the water. In most instances, water constitutes from 30 to 90 percent by weight of the reaction mixture. Frequently water constitutes from 35 to 75 percent by weight of the reaction mixture. From 40 to 60 percent by weight is preferred.

A water-miscible organic cosolvent such as tetrahydrofuran may be present in the reaction mixture, but it is preferred that the reaction mixture be free of organic cosolvent.

The temperature at which the reaction of step (a) may be conducted may also be widely varied. In many instances the temperature is in the range of from 0° C. to 100° C. Often the temperature is in the range of from 0° C. to 80° C. From 10° C. to 60° C. is preferred.

Although it is not desired to be bound by any theory, it is believed that the reaction of step (a) produces several aliphatic species. It is also believed that water removal as well as heating is necessary in step (b) to achieve dehydration leading to cyclization and the production of N-hydroxysuccinimide, at least in good yields.

The temperature to which the reaction mixture is heated in step (b) may vary widely. The temperature should not be so high as to cause significant decomposition and/or discoloration of the product. Ordinarily the temperature is in the range of from 50° C. to 200° C. In many cases the temperature is in the range of from 70° C. to 150° C. From 90° C. to 130° C. is preferred.

The temperature at which water is removed from the reaction mixture in step (b) may also vary widely. Again, the temperature should not be so high as to cause significant decomposition and/or discoloration of the product. Usually the temperature is in the range of from 50° C. to 200° C. Frequently the temperature is in the range of from 70° C. to 150° C. From 90° C. to 130° C. is preferred.

The pressure at which water removal is accomplished in step (b) is also susceptible to wide variation. In general, the pressure may be subatmospheric, ambient atmospheric, or superatmospheric. The rate of water removal at a given temperature is enhanced by using subatmospheric pressures. Usually the pressure is in the range of from 0.1 to 101 kilopascals, absolute. Often the pressure is in the range of from 1 to 50 kilopascals, absolute. From 1 to 10 kilopascals, absolute, is preferred. For convenience ambient atmospheric pressure is often used.

Water removal can also be enhanced by purging the reactor with an inert gas such as nitrogen during the heating.

The amount of water used to dissolve the solid in step (c) is susceptible to very wide variation. In general, the amount of water present should be sufficient to dissolve the solid. The maximum amount of water is not limited by theory, but by practical considerations such as the size of equipment and the costs of handling the water. In most instances, water constitutes from 30 to 90 percent by weight of the aqueous solution. Frequently water constitutes from 35 to 75 percent by weight of the aqueous solution. From 40 to 60 percent is preferred.

A water-miscible organic cosolvent such as tetrahydrofuran may be present in the aqueous solution produced in step (c), but it is preferred that the aqueous solution be free of organic cosolvent.

The substantially water-immiscible inert organic solvent ("good organic solvent") may be any organic solvent in which the acylating agent and the N-(organocarbonyloxy)succimide dissolve in significant amounts under the conditions of use. Factors having a bearing on suitability include the identities of both the acylating agent and the N-(organocarbonyloxy)succinimide, and the temperature. Examples of good organic solvents which are useful include methyl acetate, ethyl acetate, propyl acetate, butyl acetate, ethyl propionate, diethyl ether, methyl tert-butyl ether, benzene, toluene, xylene, methylene chloride, and chloroform.

The relative amounts of good organic solvent and aqueous solution combined in step (d) may vary considerably. Often the weight ratio of good organic solvent to aqueous solution in the two-phase liquid system is in the range of from 0.5:1 to 2:1. Frequently the weight ratio is in the range of from 0.7:1 to 1.5:1. From 0.8:1 to 1.2:1 is preferred.

The addition of acylating agent in step (e) may be made before and/or during the reaction of step (f). The addition of base in step (e) may be made before and during the reaction of step (f). In most instances the additions are made concurrently as separate streams during the reaction.

Any of a wide variety of acylating agents may be added in step (e). Examples include organic chloroformates including methyl chloroformate [CAS 79-22-1], ethyl chloroformate [CAS 541-41-3], propyl chloroformate [CAS 109-61-5], isopropyl chloroformate [CAS 108-23-6], butyl chloroformate [CAS 592-34-7], hexyl chloroformate [CAS 6092-54-2], heptyl chloroformate [CAS 33758-34-8], octyl chloroformate [CAS 7452-59-7], decyl chloroformate [CAS 55488-51-2], dodecyl chloroformate [CAS 24460-74-0], octadecyl chloroformate [CAS 51637-93-5], cyclohexyl chloroformate [CAS 13248-54-9], cycloheptyl chloroformate [CAS 33670-07-4], cyclooctyl chloroformate [CAS 58906-69-7], cyclohexylmethyl chloroformate [CAS 6099-86-1], phenyl chloroformate [CAS 1885-14-9], benzyl chloroformate [CAS 501-53-1], 9-fluorenylmethyl chloroformate [CAS 28920-43-6], ethylene glycol bis(chloroformate) [CAS 124-05-0], diethylene glycol bis(chloroformate) [CAS 106-75-2], 1,4-cyclohexanediyl bis(chloroformate) [CAS 18753-97-4], 1,4-cyclohexanediylbis(methylene) bis(chloroformate) [CAS 2916-24-7], and bisphenol A bis(chloroformate) [CAS 2024-88-6]. Other examples include organic acid chlorides including acetyl chloride [CAS 75-36-5], propionyl chloride [CAS 79-03-8], butanoyl chloride [CAS 141-75-3], hexanoyl chloride [CAS 142-61-0], octanoyl chloride [CAS 111-64-8], nonanoyl chloride [CAS 764-85-2], decanoyl chloride [CAS 112-13-0], dodecanoyl chloride [CAS 112-16-3], tetradecanoyl chloride [CAS 112-64-1], octadecanoyl chloride [CAS 112-76-5], benzoyl chloride [CAS 98-88-4], phenylacetyl chloride [CAS 103-80-0], malonyl dichloride [CAS 1663-67-8], succinyl dichloride [CAS 543-20-4], adipoyl dichloride [CAS 111-50-2], sebacoyl dichloride [CAS 111-19-3], phthaloyl dichloride [CAS 88-95-9], isophthaloyl dichloride [CAS 99-63-8], and terephthaloyl dichloride [CAS 100-20-9]. A single acylating agent or a mixture of acylating agents may be used as desired.

The molar ratio of the acylating agent added in step (e) to the NHS present in the liquid system may vary considerably. Often the molar ratio is in the range of from 0.8:1 to 1.2:1. In many instances the molar ratio is in the ratio of from 0.9:1 to 1.1:1. From 0.95:1 to 1.05:1 is preferred.

Base is added to the liquid system in step (e) so as to establish and maintain the pH of the aqueous phase in the desired range of pH during the reaction of step (f). In most cases the pH of the aqueous phase during the reaction is in the range of from 4 to 12. Often the pH is in the range of from 5 to 9. From 6 to 8 is preferred.

The temperature at which the reaction of step (f) is conducted may vary widely. Usually the temperature is in the range of from 0° C. to 50° C. Frequently the temperature is in the range of from 5° C. to 30° C. From 10° C. to 20° C. is preferred.

Preferably N-(organocarbonyloxy)succinimide is precipitated from the organic phase in which it has accumulated.

Precipitation of the N-(organocarbonyloxy)succinimide from the organic phase may be accomplished by cooling the organic phase and/or by distilling good solvent from the organic phase.

When good organic solvent is distilled from the organic phase, the temperature of the distillation may also vary widely. Again, the temperature should not be so high as to cause significant decomposition and/or discoloration of the product. Usually the temperature is in the range of from 50° C. to 150° C. Frequently the temperature is in the range of from 70° C. to 120° C. From 75° C. to 100° C. is preferred.

The pressure at which distillation of the good organic solvent is accomplished is also susceptible to wide variation. In general, the pressure may be subatmospheric, ambient atmospheric, or superatmospheric. The rate of removal of good organic solvent at a given temperature is enhanced by using subatmospheric pressures. Usually the pressure is in the range of from 0.1 to 101 kilopascals, absolute. Often the pressure is in the range of from 1 to 50 kilopascals, absolute. From 1 to 10 kilopascals, absolute, is preferred. For convenience ambient atmospheric pressure is often used.

Preferably, the basic method of the invention described above further comprises: (a) separating the liquid aqueous phase from the liquid organic phase containing the N-(organocarbonyloxy)succinimide; (b) optionally distilling a portion of the substantially water-immiscible inert organic solvent from the separated organic phase; (c) combining the remaining liquid organic phase and inert organic liquid which is miscible with the substantially water-immiscible inert organic solvent but which is a poor solvent for the N-(organocarbonyloxy)succinimide, to form an organic liquor; (d) cooling the organic liquor to precipitate N-(organocarbonyloxy)succinimide crystals and to produce a mother liquor; and (e) separating precipitated N-(organocarbonyloxy)succinimide crystals from the mother liquor.

Separation of the liquid aqueous phase from the liquid organic phase may be accomplished by any technique of liquid-liquid phase separation well known to the art such as for example, decantation, drainage of the lower layer, and centrifugation.

When a portion of the good organic solvent is distilled from the separated organic phase, the conditions of temperature and pressure are suitably as stated above.

The organic liquid which is miscible with the good organic solvent but which is a poor solvent for the N-(organocarbonyloxy)succinimide ("poor organic solvent") may be any organic solvent which reduces the solubility of the solute in the good organic solvent. Preferably, the poor organic solvent is miscible in all proportions with the good organic solvent. The general principles of using good solvent-poor solvent pairs to precipitate substances from solution are well known, as is the selection of good solvent-poor solvent pairs; see Kirk-Othmer, *Encyclopedia of Chemical Technology*, 2d Edition, Volume 6, John Wiley & Sons, New York, page 506 (1965). An example of a good organic solvent-poor organic solvent pair is ethyl acetate and isopropanol. Another is ethyl acetate and heptane. Factors having a bearing on suitability include the identity of the good organic solvent, the identity of the poor organic solvent, the identity of the N-(organocarbonyloxy)succinimide, and the temperature.

The precipitated N-(organocarbonyloxy)succinimide crystals may be separated from the mother liquor by any conventional procedure such as decantation, filtration, or centrifugation.

Alternatively, the basic method of the invention further comprises: (a) separating the liquid aqueous phase from the liquid organic phase containing the N-(organocarbonyloxy)succinimide; and (b) distilling at least a portion of the substantially water-immiscible inert organic solvent from the separated organic phase to precipitate N-(organocarbonyloxy)succinimide crystals.

Phase separation may be accomplished as described above. The conditions for distillation as described above are satisfactory for this embodiment. If desired, the distillation may be continued to dryness. It is preferred however that only a portion of the good solvent be distilled so that a mother liquor remains. The precipitated N-(organocarbonyloxy)succinimide crystals may be separated from the mother liquor by any conventional technique, as described above. The mother liquor may be processed to recover a second crop of crystals or it may be recycled to the basic process at step (d) or between steps (f) and (g).

In another embodiment of the basic method of the invention, the reaction mixture is acidified with strong acid and then water is removed from the acidified reaction mixture to produce solid comprising N-hydroxysuccinimide and a contaminating amount of succinic acid. As used herein, strong acid is an acid that is stronger than succinic acid. Examples of strong acids include sulfuric acid, hydrochloric acid, nitric acid, and phosphoric acid. A single strong acid or a mixture of two or more strong acids may be used as desired.

The invention is further described in conjunction with the following examples which are to be considered illustrative rather than limiting, and in which all parts are parts by weight and all percentages are percentages by weight unless otherwise specified. In calculating yields, analyses determined by chromatography and expressed as area percents, are taken as weight percents.

EXAMPLE 1

Hydroxylamine sulfate in the amount of 131.0 grams was charged to a 2-liter, 3-necked reactor equipped with a mechanical stirrer, temperature controller, nitrogen inlet, and distillation assembly. To this was added with stirring 128 grams of a solution of 50% aqueous sodium hydroxide in 236 milliliters of water. One hundred 100 milliliters of water was used to rinse a sodium hydroxide container and the resulting dilute solution was added to the reactor. The reaction mixture was stirred until most solids had dissolved and then cooled in ice to 12° C. One hundred fifty grams of succinic anhydride was added in 5 installments. The reaction mixture was stirred until the succinic anhydride dissolved after each addition while keeping the temperature below 20° C. After the addition the reaction mixture was allowed to warm to room temperature. The reaction mixture was then heated to 45° C. A solution of 3.8 grams of concentrated sulfuric acid in 20 milliliters of water was added. Heating was continued under nitrogen flow to distill out water. After the temperature reached 140° C. this temperature was maintained for 2½ hours under nitrogen. The resulting solids were cooled to 45° C. and then 450 milliliters of the water which had previously removed by distillation and 150 milliliters of fresh water were added. The reaction mixture was stirred at 45° C. to dissolve the solids. After the solids had dissolved, the solution was cooled to 15° C. and 120 grams of 50 percent aqueous sodium hydroxide diluted with 140 milliliters of cold water was added. The pH was 7.5. The reaction mixture was allowed to stand overnight at about 10° C. The next day an additional 12.0 grams of 50 percent aqueous sodium hydroxide solution was added to adjust the pH of the reaction mixture to 8.8. Five hundred fifty milliliters of ethyl acetate was added and the reaction mixture was stirred well. The temperature of the reaction mixture was 12° C. Twenty milligrams of trimethyl C8-C10 quaternary ammonium chloride (Adogen ® 464; Sherex Chemical Co.) was added. From an addition funnel 221.0 grams of benzyl chloroformate was added dropwise over a period of one hour. The temperature was maintained at 15° C. during the addition. After the addition the pH was 7.3 which was adjusted to 7.8 with an additional 4 grams of 50 percent aqueous sodium hydroxide solution. The cooling bath was removed and the reaction mixture was stirred while the temperature increased to room temperature. After one hour the temperature was 20° C. and the pH was about 6.6. The pH was adjusted to 7.3 with about 4 grams of 50 percent aqueous sodium hydroxide solution. The reaction mixture was then stirred at from 20° C. to 22° C. for one hour. Some crystals were observed in the aqueous phase. The reaction mixture was warmed to 30° C. in a hot water bath. Both phases were now clear. The organic phase was separated and stirred over 30 grams of magnesium sulfate and 3 grams of charcoal. Solids were then removed by filtration and washed with about 100 milliliters of ethyl acetate. This ethyl acetate was combined with the earlier separated organic phase. The resulting ethyl acetate solution weighed 860 grams. Ten grams of the solution when stripped yielded 3.61 grams of solids. The ethyl acetate solution was heated at 20 kilopascals, absolute, in a 50° C. bath to remove about 385 grams of ethyl acetate. To the remaining solution was added about 70 milliliters of heptane (until the solution became cloudy) and the mixture was cooled to 25° C. undisturbed. An additional 70 milliliters of heptane was added. The flask containing the mixture was allowed to stand in a refrigerator for one hour. At the conclusion of that time the temperature of the mixture was 18° C. and crystals had formed. The crystals were hard lumps which were broken up and then filtered. The crystals were washed twice with 50 milliliters of 50 percent heptane:50 percent ethyl acetate solution and dried. The weight of the crystals was 256.0 grams. Analysis by high pressure liquid chromatography ("HPLC") showed the crystals to be 99 area percent BCS.

The remaining filtrate was stripped in vacuo to obtain 52 grams of light yellow syrup that was diluted with 35 milliliters of ethyl acetate and 25 milliliters of heptane. Initially two liquid phases were present. The solution was then cooled in the refrigerator overnight. As crystals separated, only one liquid phase remained. The crystals were filtered and washed with 50 percent heptane:50 percent ethyl acetate solution and dried. The weight of the crystals was 32 grams. Analysis by HPLC showed the second crop of crystals to be 97.8 area percent BCS and about 2 area percent unknown.

The second crop of crystals was redissolved in 30 milliliters of ethyl acetate with warming. The solution was cooled to room temperature and then to 0° C. to precipitate crystals. The crystals were filtered, washed with 50 percent heptane:50 percent ethyl acetate solution, and dried. The weight of the crystals was 14.8 grams. Analysis by HPLC showed the crystals to be about 98 area percent BCS.

The remaining mother liquor was stripped to 20 grams weight and 5 milliliters of ethyl acetate was added. The solution was seeded with BCS and allowed to stand at room temperature. Some crystals separated, but the purity was only 80 area percent.

Yield of the first crop and the recrystallized second crop combined was 71.7 percent based on succinic anhydride.

EXAMPLE 2

A one-liter, 3-necked reaction flask equipped with mechanical stirrer, temperature controller, and distillation assembly, was charged with 90.5 grams of hydroxylamine sulfate. A solution of 88 grams of a solution of 50% aqueous sodium hydroxide in 200 milliliters of cold water was then added with stirring. The reaction mixture was stirred to dissolve all crystals and then cooled to 10° C. The pH of the reaction mixture was 12.0. One hundred grams of succinic anhydride was added in 5 installments. The temperature was maintained in the range of from 15° C. to 20° C. during the addition. After the addition had been completed, the reaction mixture was stirred at temperatures in the range of from 10° C. to 15° C. until most of the succinic anhydride had dissolved. The reaction mixture was warmed to room temperature and then heated under nitrogen to distill water out. Most of the water had distilled out at pot temperatures of from 105° C. to 115° C. The mixture was then gradually heated to 130° C. and maintained at 130° C. under nitrogen flow for 2 hours. The flask was evacuated to a pressure of 2 kilopascals, absolute and held at 130° C. for ½ hour. The reaction mixture was cooled, and at 60° C. the product began to solidify. Two hundred thirty grams of the water that had previously been removed by distillation was returned to the flask. The reaction mixture was stirred to dissolve the solids while cooling to 10° C. A solution of 88.0 grams of 50% aqueous sodium hydroxide in 100 milliliters of water was then added while maintaining the temperature below 20° C. The pH at the conclusion of the addition was 11.3. Three hundred fifty milliliters of ethyl acetate was added and the reaction mixture was cooled to 10° C. One hundred fifty grams of benzyl chloroformate was added over a period of about one hour. The mixture was then stirred for one hour at 15° C. Crystallization was noticed and therefore 200 milliliters of water was added. The pH of the aqueous phase was adjusted to 8.5 with 50% aqueous sodium hydroxide and the reaction mixture was stirred overnight at room temperature. The yellow organic phase was separated from the aqueous phase, treated with a scoop of activated charcoal, and filtered through Celite ® diatomaceous earth filter aid (Celite Corp.). The filtered organic solution was then concentrated in vacuo to a weight of 305 grams. Heptane was added until the mixture began to cloud up at about 70° C. The mixture was cooled with stirring to room temperature and then in an ice-water bath to 10° C. The crystals which had formed were removed by filtration and washed with 100 milliliters of 50 percent heptane:50 percent ethyl acetate solution and dried. The weight of the resulting first crop of crystals was 132.0 grams. The mother liquor was concentrated in vacuo and the residue was dissolved in 100 milliliters of 50 percent heptane:50 percent ethyl acetate solution. The mixture was cooled in a refrigerator for several hours and filtered. The crystals which had formed were washed with 50 percent heptane:50 percent ethyl acetate solution and dried. The resulting second crop of crystals weighed 17.0 grams. The two crops were combined to obtain 149 grams of crystals as product. HPLC showed the product to be BCS having a purity of greater than 99 area percent. The yield was 59.2 percent based on succinic anhydride.

EXAMPLE 3

A five-liter, 3-necked reaction flask equipped with mechanical stirrer, nitrogen inlet, temperature controller, and distillation assembly, was charged with 258 grams of hydroxylamine sulfate. A solution of 126 grams of sodium hydroxide in 650 milliliters of water was then added. The reaction mixture was stirred to dissolve all crystals. The temperature of the solution was 22° C. To the stirred solution was added 300 grams of succinic anhydride. The reaction was slightly exothermic and the temperature rose to 40° C. After the addition had been completed, the reaction mixture was stirred for ½ hour at 40° C. The reaction mixture was warmed to 60° C. and then 7.6 grams of concentrated sulfuric acid was added. Heating was continued to distill water out until the temperature reached 130° C. The reaction mixture was then maintained at 130° C. for 2 hours and then cooled to 80° C. Eight hundred milliliters of the water that had previously been removed by distillation was returned to the flask. The reaction mixture was stirred to dissolve the solids present. A caustic additive solution was made by dissolving 130 grams of sodium hydroxide in 500 milliliters of water. A portion of the caustic additive solution was then added to the reaction mixture until the pH of the reaction mixture was 6.8. The reaction mixture was diluted with a further 200 milliliters of water and allowed to stand overnight. To the reaction mixture was added 1300 milliliters of ethyl acetate. The pH of the aqueous phase was 6.6. Over a period of 2 hours 456 grams of benzyl chloroformate was added. As the addition proceeded, the pH dropped to 6.0. The pH was adjusted to 6.6 with half of the remaining caustic additive solution. As the addition of benzyl chloroformate continued, the pH again dropped to 6.0. This was adjusted to 6.6 with the remaining caustic additive solution. At the conclusion of the benzyl chloroformate addition, the pH was 5.8. The pH was raised to 6.25 with 50 percent aqueous sodium hydroxide solution. The reaction mixture was then stirred for 4½ hours at 25° C. During this period when the pH dropped to 6.0 it was adjusted each time to a pH in the range of from 6.4 to 6.5 using 50 percent aqueous sodium hydroxide solution. A total of 36.0 grams of 50 percent aqueous sodium hydroxide solution was added for pH adjustment. The reaction mixture was transferred to a separatory funnel and then allowed to stand quiescently until phase separated. The aqueous phase was drained out and the organic phase was allowed to stand overnight. The organic phase was returned to the reactor and 840 grams of ethyl acetate was distilled out. To the residue was added 1100 milliliters of isopropanol. The organic phase was heated to 70° C., cooled with stirring to 40° C., and then seeded with some BCS crystals. As crystals precipitated the temperature rose to 45° C. The mixture was gradually cooled in and ice-water bath to 10° C. After stirring for one hour, the mixture was filtered under suction. The crystals were then washed by displacement with 200 milliliters of cold isopropanol and dried in air. The dry crystals weighed 568 grams. The mother liquor and the washings were all combined and charged into a reactor. The reactor was heated to distill out 790 grams of solvent. The residue, which weighed 191 grams, was removed from the reactor, cooled in a refrigerator, and filtered. The crystals which had formed were washed with isopropanol and dried. The resulting second crop of crystals weighed 28 grams. The two crops were combined to obtain 596 grams of crystals as product. HPLC showed the product to be BCS having a purity of 99.4 weight percent. The yield of BCS product was 79.3 percent based on succinic anhydride.

Although the present invention has been described with reference to specific details of certain embodiments thereof, it is not intended that such details should be regarded as limitations upon the scope of the invention except insofar as they are included in the accompanying claims.

We claim:

1. A method for producing N-(organocarbonyloxy)-succinimide comprising:
    (a) reacting succinic anhydride with hydroxylamine in water to form a reaction mixture;
    (b) heating said reaction mixture and removing water to produce solid comprising N-hydroxysuccinimide and a contaminating amount of succinic acid;
    (c) dissolving said solid in water to form an aqueous solution comprising dissolved N-hydroxysuccinimide and dissolved succinic acid;
    (d) combining substantially water-immiscible inert organic solvent and said aqueous solution to form a two-phase liquid system having an organic phase and an aqueous phase comprising said dissolved N-hydroxysuccinimide and said dissolved succinic acid;
    (e) adding base and at least one acylating agent represented by the formula

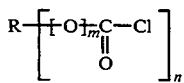

to said liquid system; and
    (f) reacting dissolved N-hydroxysuccinimide, said base, and said acylating agent in said liquid system to produce N-(organocarbonyloxy)succinimide represented by the formula

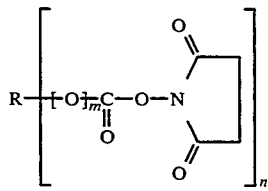

which accumulates in the organic phase; wherein R is an organo group, m is 0 or 1, and n is the valence of R.

2. The method of claim 1 wherein said organo group contains from 1 to 18 carbon atoms.

3. The method of claim 1 wherein m is 0.

4. The method of claim 1 wherein m is 1.

5. The method of claim 1 wherein the valence of R is 1.

6. The method of claim 1 wherein the valence of R is 2.

7. The method of claim 1 further comprising precipitating N-(organocarbonyloxy)succinimide from said organic phase in which it has accumulated.

8. The method of claim 1 further comprising:
    (a) separating the liquid aqueous phase from the liquid organic phase containing said N-(organocarbonyloxy)succinimide;
    (b) optionally distilling a portion of the substantially water-immiscible inert organic solvent from the separated organic phase;
    (c) combining the remaining liquid organic phase and inert organic liquid which is miscible with said substantially water-immiscible inert organic solvent but which is a poor solvent for said N-(organocarbonyloxy)succinimide, to form an organic liquor;
    (d) cooling said organic liquor to precipitate N-(organocarbonyloxy)succinimide crystals and to produce a mother liquor; and
    (e) separating precipitated N-(organocarbonyloxy)succinimide crystals from said mother liquor.

9. The method of claim 1 further comprising:
    (a) separating the liquid aqueous phase from the liquid organic phase containing said N-(organocarbonyloxy)succinimide; and
    (b) distilling at least a portion of the substantially water-immiscible inert organic solvent from the separated organic phase to precipitate N-(organocarbonyloxy)succinimide crystals.

10. The method of claim 1 wherein said reaction mixture is acidified with strong acid and wherein water is removed from the acidified reaction mixture to produce said solid.

11. The method of claim 10 wherein said strong acid is sulfuric acid, hydrochloric acid, nitric acid, phosphoric acid, or a mixture of two or more thereof.

12. The method of claim 1 wherein said hydroxylamine is produced in situ by the reaction of hydroxylamine salt and base.

13. The method of claim 12 wherein said hydroxylamine salt is hydroxylamine sulfate, hydroxylamine hydrochloride, hydroxylamine hydrobromide, hydroxylamine nitrate, hydroxylamine phosphate, or a mixture of two or more thereof.

14. The method of claim 12 wherein said base which is reacted with said hydroxylamine salt is alkali metal hydroxide, alkaline earth metal hydroxide, or a mixture thereof.

15. A method for producing N-(benzyloxycarbonyloxy)succinimide comprising:
    (a) reacting succinic anhydride with hydroxylamine in water to form a reaction mixture;
    (b) heating said reaction mixture and removing water to produce solid comprising N-hydroxysuccinimide and a contaminating amount of succinic acid;
    (c) dissolving said solid in water to form an aqueous solution comprising dissolved N-hydroxysuccinimide and dissolved succinic acid;
    (d) combining substantially water-immiscible inert organic solvent and said aqueous solution to form a two-phase liquid system having an organic phase and an aqueous phase comprising said dissolved N-hydroxysuccinimide and said dissolved succinic acid;

(e) adding base and benzyl chloroformate to said liquid system; and (f) reacting dissolved N-hydroxysuccinimide, said base, and said benzyl chloroformate in said liquid system to produce N-(benzyloxycarbonyloxy)succinimide which accumulates in the organic phase.

16. A method for producing N-(9-fluorenylmethoxycarbonyloxy)succinimide comprising:

(a) reacting succinic anhydride with hydroxylamine in water to form a reaction mixture;

(b) heating said reaction mixture and removing water to produce solid comprising N-hydroxysuccinimide and a contaminating amount of succinic acid;

(c) dissolving said solid in water to form an aqueous solution comprising dissolved N-hydroxysuccinimide and dissolved succinic acid;

(d) combining substantially water-immiscible inert organic solvent and said aqueous solution to form a two-phase liquid system having an organic phase and an aqueous phase comprising said dissolved N-hydroxysuccinimide and said dissolved succinic acid;

(e) adding base and 9-fluorenylmethyl chloroformate to said liquid system; and (f) reacting dissolved N-hydroxysuccinimide, said base, and said 9-fluorenylmethyl chloroformate in said liquid system to produce N-(9-fluorenylmethoxycarbonyloxy)succinimide which accumulates in the organic phase.

* * * * *